United States Patent
Nie et al.

(10) Patent No.: US 11,561,215 B2
(45) Date of Patent: Jan. 24, 2023

(54) SCALE-COUPLED MULTISCALE MODEL SIMULATION

(71) Applicant: Halliburton Energy Services, Inc., Houston, TX (US)

(72) Inventors: Xiaobo Nie, Richmond, TX (US); Jonas Toelke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 350 days.

(21) Appl. No.: 16/670,974

(22) Filed: Oct. 31, 2019

(65) Prior Publication Data

US 2021/0132026 A1    May 6, 2021

(51) Int. Cl.
*G01N 33/24*  (2006.01)
*G01N 23/046*  (2018.01)
*G06F 30/20*  (2020.01)

(52) U.S. Cl.
CPC ........... *G01N 33/24* (2013.01); *G01N 23/046* (2013.01); *G06F 30/20* (2020.01)

(58) Field of Classification Search
CPC ....... G01N 33/24; G01N 23/046; G06F 30/20
USPC .......................................................... 703/10
See application file for complete search history.

(56) References Cited

U.S. PATENT DOCUMENTS

| | | | |
|---|---|---|---|
| 6,453,727 B1 | 9/2002 | Lenormand et al. | |
| 6,516,080 B1 | 2/2003 | Nur | |
| 8,908,925 B2 | 12/2014 | Hurley et al. | |
| 9,134,457 B2 | 9/2015 | Hurley et al. | |
| 9,183,326 B2 | 11/2015 | De Prisco et al. | |
| 9,507,047 B1 | 11/2016 | Dvorkin et al. | |
| 2012/0281883 A1* | 11/2012 | Hurley | G01N 21/6458 382/109 |
| 2016/0124115 A1 | 5/2016 | Theologou et al. | |
| 2019/0026405 A1 | 1/2019 | Ramsay et al. | |

OTHER PUBLICATIONS

Grigo_2019 (A Physics-aware, probabilistic machine learning framework for coarse-graining high-dimensional systems in the small data regime, research gate Feb. 2019) (Year: 2019).*
Jiang_2013 (Representation of multiscale heterogeneity via multiscale pore networks 2013). (Year: 2013).*
Shikhov_2015 (Evaluation of Capillary Pressure Methods via Digital Rock Simulation, 2015) (Year: 2015).*

(Continued)

*Primary Examiner* — Brian S Cook
(74) *Attorney, Agent, or Firm* — DeLizio, Peacock, Lewin & Guerra

(57) ABSTRACT

Overlapping pores in a multiscale model of heterogeneous core formation contributes errors during flow simulations. A scale-coupled multiscale modeling that corrects for contributions of overlapping pores may be used to determine capillary pressure and relative permeability of the heterogenous core formation more accurately. The effects of overlapping pores may be removed by converting pores that have a certain radius or are filled with certain fluids into solid regions. The effects of overlapping pores may also be removed by running flow simulations on a modified model and correcting various fluid properties of the core formation with the results.

23 Claims, 11 Drawing Sheets

(56) References Cited

OTHER PUBLICATIONS

Martinez_2018 (Minkowski Functionals of Connected Soil Porosity as Indicators of Soil Tillage and Depth, 13, Jun. 2018) (Year: 2018).*

De Prisco, et al., "Computation Of Relative Permeability Functions In 3D Digital Rocks By A Fractional Flow Approach Using The Lattice Boltzmann Method", International Symposium Of The Society Of Core Analysis, Aug. 2012, 12 pages.

PCT Application Serial No. PCT/US2019/059276, International Search Report, dated Jul. 27, 2020, 3 pages.

PCT Application Serial No. PCT/US2019/059276, International Written Opinion, dated Jul. 27, 2020, 7 pages.

Jiang, et al., "Representation of Multiscale Heterogeneity via Multiscale Pore Networks", Water resources research, vol. 49, No. 9, 2013, 13 pages.

* cited by examiner

SCALE-COUPLED MULTISCALE MODEL SIMULATION

TECHNICAL FIELD

The disclosure generally relates to the field of investigating or analyzing materials by determining their chemical or physical properties (G01N) and to determining capillary pressure and relative permeability of core samples, and thereby of a subterranean formation.

BACKGROUND

During oil and gas exploration and production, reservoir core or core samples are taken out from the field and analyzed to determine the petrophysical properties of the subterranean formation. Core analysis of a sample from a borehole in a subterranean formation provides a means of measuring downhole conditions to determine formation properties such as input porosity, absolute permeability, capillary pressure, and relative permeability. Core analysis is useful for well log calibration and providing direct evidence of the presence, distribution, and deliverability of hydrocarbons. Moreover, core analysis provides important information useful to determine the optimal values for various parameters during formation drilling and hydrocarbon production, such as when to drill, what target depth to set fracturing, which wells to inject with fluids, etc. Determination of various material properties of the core may also be a part of reservoir modeling or simulation which is a process of creating a digital representation of the reservoir. Such simulation of the reservoir aids in various stages of the drilling process including well planning to well abandonment.

Various properties of the subterranean core formation are required to create simulations of the reservoir that are able to predict the location of hydrocarbons and improve drilling production. They include input porosity, absolute permeability, capillary pressure, relative permeability, and others. Two of the properties, capillary pressure and relative permeability, are typically obtained by physical laboratory experiments performed on a sample core or plug of core, such as porosimetry, nuclear magnetic resonance techniques, and gas adsorption techniques. These processes however can be costly and time consuming.

BRIEF DESCRIPTION OF THE DRAWINGS

Embodiments of the disclosure may be better understood by referencing the accompanying drawings.

DESCRIPTION OF EMBODIMENTS

Figure 1:
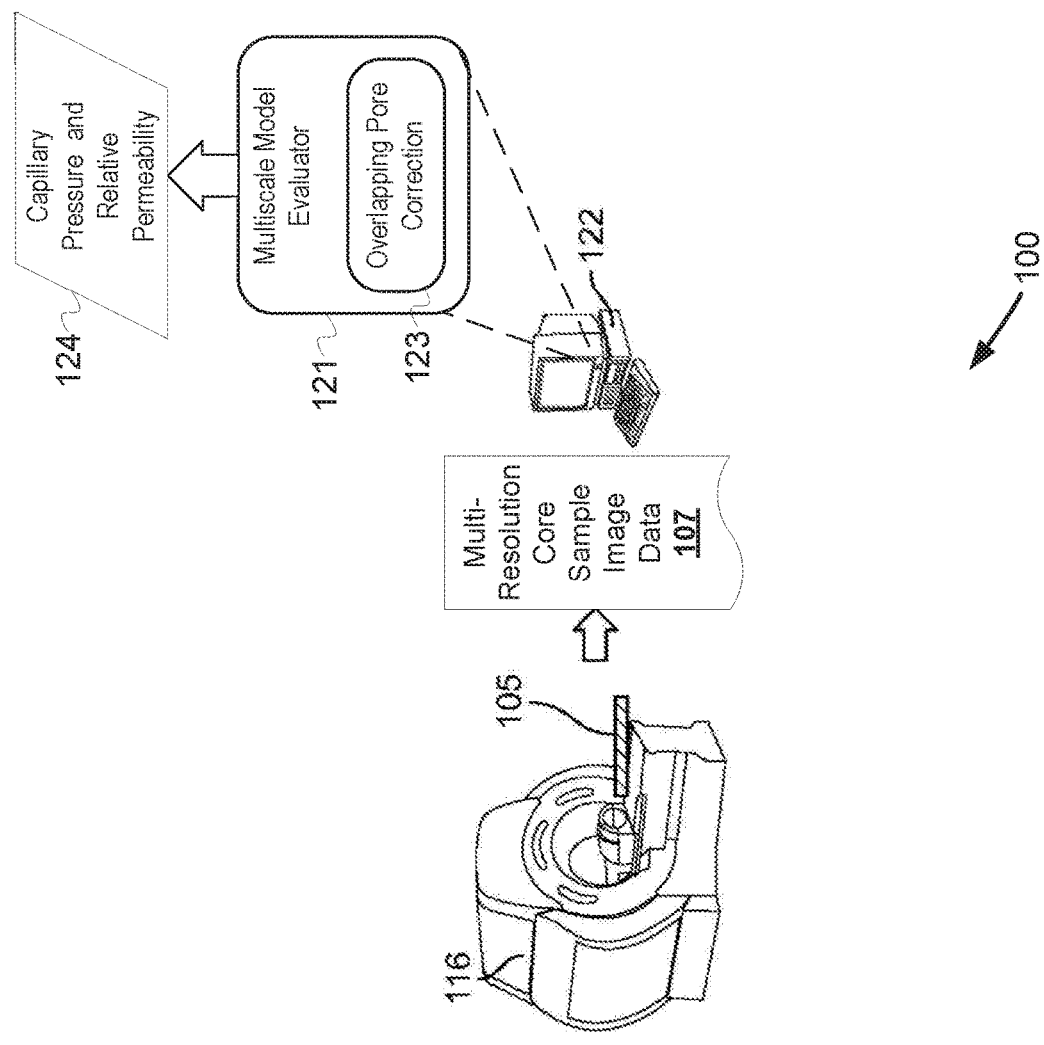
FIG. 1 depicts an example system for collecting and imaging core samples used for multiscale modeling to determine capillary pressure and relative permeability.
Figure 1:
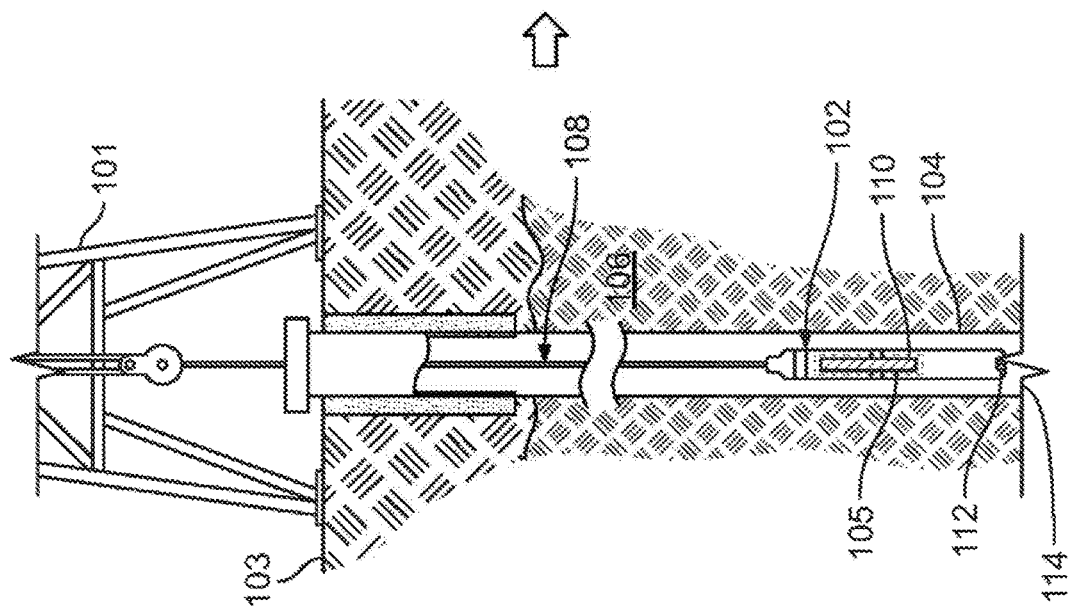

The description that follows includes example systems, methods, techniques, and program flows that support embodiments of the disclosure. However, it is understood that this disclosure may be practiced without these specific details. For instance, this disclosure refers to determining an opening map with a Minkowski functional in illustrative examples. Aspects of this disclosure can also be applied to other morphological algorithms. In other instances, well-known instruction instances, protocols, structures, and techniques have not been shown in detail in order not to obfuscate the description.

Overview

Reservoir simulation is performed with a variety of formation describing models and measurements, including capillary pressure and relative permeability. Different formation evaluation techniques are used to determine the formation describing models and measurements. There are three formation evaluation techniques that can be used to obtain capillary pressure curves for a core: porous plate, centrifuge, and mercury intrusion porosimetry. Formation evaluation using a porous plate experiment is considered the most accurate approach as it avoids creating a saturation gradient and operates using native fluids. Moreover, results of a porous plate experiment can be combined with other measurements of the core to conduct an expanded analysis. However, a porous plate experiment is a time-consuming method that may require weeks to obtain an accurate oil-water drainage curve. Using a digital experiment, instead of a physical experiment to inform formation evaluation, would determine capillary pressure and relative permeability of the formation more efficiently and effectively and increase accuracy of a reservoir simulation.

The complexity of a heterogeneous formation includes continuous pores of different scales that can range from nanometers to microns and fractal rock features. To capture this complexity and efficiently determine capillary pressure and relative permeability, a scale-coupled multiscale model evaluator with overlapping pore correction has been designed. With image data of a core sample at different resolutions, a model of the core sample can be generated that couples the dynamic formation characteristics of different scales. While the dynamic characteristics could be determined for the different scales with separate model simulations, the dynamic characteristics can be more accurately reflected with scale coupling in a model because the multiscale model would capture the interactions throughout the heterogeneous formation. With scale coupling, there will be pore overlapping (i.e., occurrence of the same pores at the same spatial location in different images of different resolutions). This pore overlapping contributes errors. Thus, the scale-coupled multiscale model evaluator removes the contributions from pore overlapping. A simulation can then be run with the multiscale model to obtain capillary pressure and relative permeability.

Example Well System

FIG. 1 depicts an example system for collecting and imaging core samples used for multiscale modeling to determine capillary pressure and relative permeability. In FIG. 1, a coring and sample analysis system 100 comprises a coring tool 102. The coring tool 102 is placed in a wellbore 104 by a rig 101 penetrating a subterranean formation 106 by a conveyance, illustrated as a wireline 108 conveyance. The coring tool 102 includes a core holder 110 and corehead 112. The corehead 112 drills through the bottom of the wellbore 114 to deposit a core sample 105 of the subterranean formation 106 into the core holder 110, which is then transported to the surface 103 for analysis. The coring tool 102 can be placed in the wellbore 104 by a different conveyance (e.g., coil tubing, wired coiled tubing, slickline, and the like) that is connected to the surface 103.

After obtaining a core sample 105, the core sample 105 is digitized at different scales of measurement. The sample analysis system 100 includes a CT scanner 116 that produces image data 107 ("image") for the internal structure of the core sample 105 at different resolutions (e.g., cross sectional image). The image can include "coarse" image data from micro-computerized tomography (CT) imaging at a first resolution and "fine" image data acquired with a higher resolution of micro-CT imaging or nano-CT acquisition. The images can include various degrees of coarse and fine images obtained at various resolutions. A computer 122 is programmed with a program 121 ("multiscale model evaluator") to perform multiscale modeling with the image data at different resolutions and a digital experiment. The multiscale model evaluator 121 includes program code 123 ("overlapping pore correction") to remove extra contributions due to pore overlapping. The multiscale model evaluator 121 then generates data 124 that includes capillary pressure and the relative permeability of the multiscale heterogamous core.

Modifications, additions, or omissions may be made to the example system 100 described in FIG. 1 without departing from the scope of the present disclosure. For example, the coring tool 102 can include a sidewall coring tool where the core samples would be removed from the side of the wellbore 104 from a hole that has already been drilled. Sidewall coring may involve firing a hollow bullet into the sidewall core formation of the drilled hole to create a core sample. Moreover, components can be added to or removed from the system 100 without departing from the scope of the present disclosure. For example, a ball check valve, swivel assembly, stabilizer, shoe assembly, and various coreheads types, such as thermally stable polycrystalline (TSP) corehead, full diamond impregnation coreheads, polycrystalline diamond compact (PDC) coreheads may be added.

In one or more embodiments, the coring and sample analysis system 100 may not use any coring device to obtain the core sample, but rather substitutes drilling cuttings for the core samples. Drilling cuttings may be obtained through a drilling string comprised of drill pipe, bottom-hole assembly, bit, and others. The subterranean layer of a certain position associated with the drilling cuttings can be determined through measuring the duration, logging-while-drilling (LWD) well logs, and other information obtained through a wireline tool.

Example Operations

The description refers to a "multiscale model evaluator" as performing the example operations. The moniker "multiscale model evaluator" is used for convenience as the operations are performed by a program or programs executed/interpreted by a device. When coupling models of different scales, the coupling leads to pore overlapping which decreases accuracy of simulations performed to determine relative permeability and capillary pressure. The flowcharts depicted in FIGS. 2-8 illustrate example operations that address the pore overlapping differently.

Figure 2:
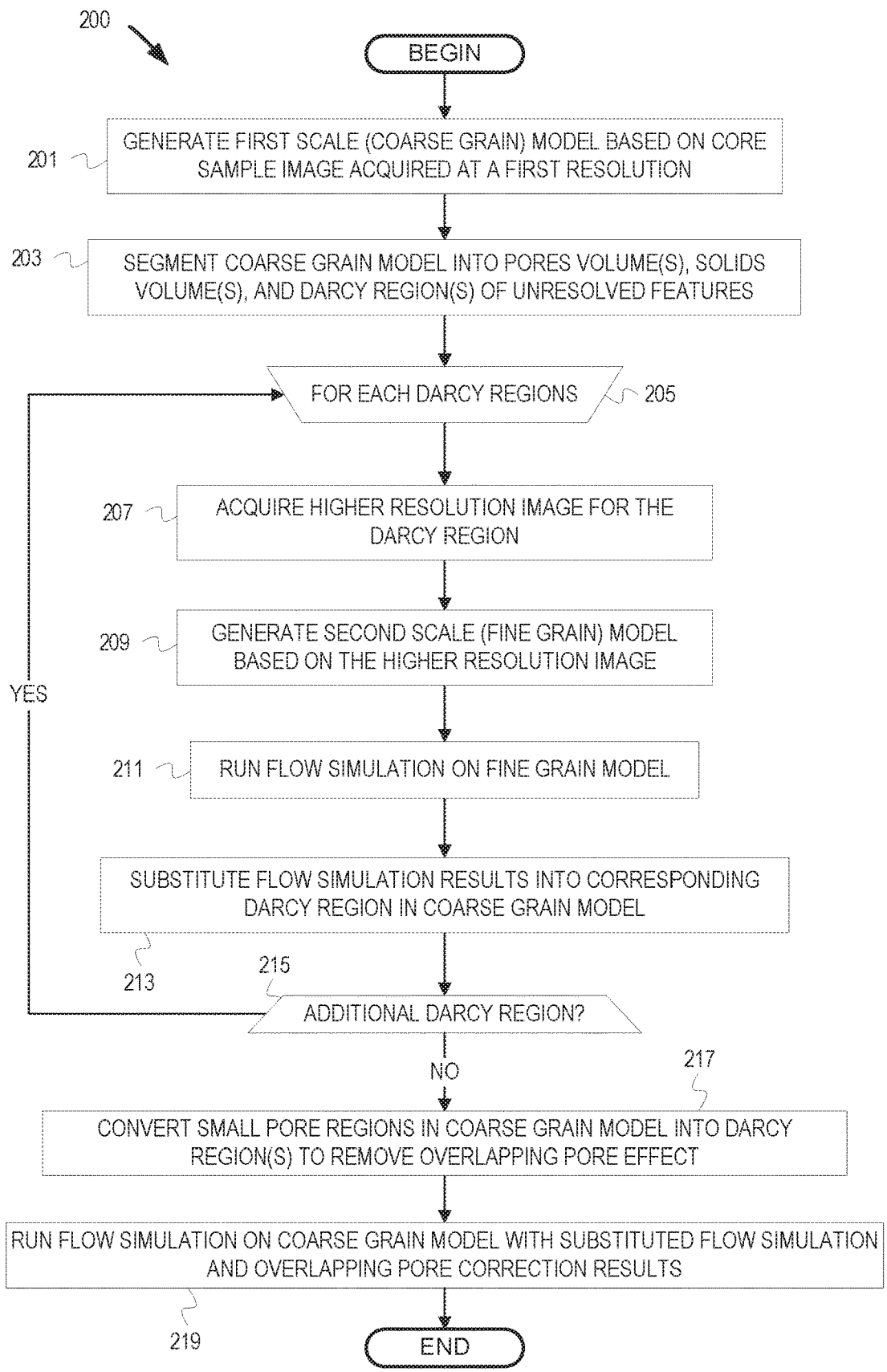
FIG. 2 depicts a flowchart of operations for multiscale modeling that removes the effect of overlapping pores for multiscale heterogeneous core formation by converting small pore regions into Darcy regions.

FIG. 2 depicts a flowchart 200 of operations for multiscale modeling that removes the effect of overlapping pores for multiscale heterogeneous core formation by converting small pore regions into Darcy regions.

At block 201, a multiscale model evaluator ("model evaluator") generates a first scale model based on a core sample image acquired at a first resolution. The core sample image is similar to that described in FIG. 1 where the image contains internal structure of the core sample imaged at different scales of measurement. Model evaluator generates the first scale model ("coarse grain model") by using a "coarse" image obtained at a first resolution. The first resolution is less than the resolution of a "fine" image with a higher resolution. Pores and pore throats may be extracted from the image by various methods including but not limited to the erosion method, the medial axis (MA) method, and the maximal ball (MB) method.

At block 203, the model evaluator segments the coarse grain model into pore volumes, solid volumes, and a Darcy region(s) of unresolved features. This operation may be incorporated into model generation (block 201), with each voxel of the coarse grain model identified as pore volume, solid volume, or Darcy region and segmented into distinct regions as it is being generated. Pore volumes are voxels of the model that are empty or void whereas solid volumes are voxels that are of solid phase. The model evaluator generates the coarse grain model in part by simulating oil and water flow through pores and possible Darcy regions based on the governing equations of fluid mechanics. Darcy regions are voxels that were unresolved as either a pore volume or a solid volume at the first resolution. Regions of unresolved features are labeled as Darcy region as they are regions that are characterized by Darcy's law which describes the flow of a fluid through a porous medium. The Darcy regions are described by map functions such as capillary pressure and relative permeability as functions of water saturations. The two-phase flow properties in a Darcy region are described by prescribed map functions. The map functions describe the macroscopic state of a fluid of the Darcy region, such as relative permeability and capillary pressure. Additionally, the model evaluator identifies the pore sizes in the coarse image by obtaining an opening map of the image. The model evaluator obtains the opening map of the core sample models by using a morphological operator corresponding to the opening morphology. For example, a Minkowski functional corresponding to the opening morphological operator may be used. The formation evaluator then identifies the size of the maximum inscribed sphere for each pore voxel and determines the pore size distribution (PSD) by counting the number of similarly sized pore voxel.

At block 205, the model evaluator begins iterating over each identified Darcy region. For each Darcy region that was identified at block 203, the model evaluator performs the operations described at blocks 207-215. The description refers to a current iteration of a Darcy region as the "selected" Darcy region.

At block 207, the model evaluator acquires a higher resolution image for the determined portion of the selected Darcy region. The higher resolution image may be acquired with a higher resolution of micro-CT imaging or nano-CT acquisition. A higher resolution image need not meet a certain threshold resolution; the resolution must only be higher relative to the first resolution. The increase in resolution may range from minimal to significant based on maximum resolution of the CT scanner, available computation resources, and accuracy of the final simulation desired.

At block 209, the model evaluator generates a second scale model ("fine grain model") based on the acquired higher resolution image. The fine grain model can be generated in an operation analogous to the operation described at blocks 201 and 203. Additionally, the model evaluator identifies the pore sizes in the fine image by obtaining an opening map of the image similar to the operation described at block 203. The model evaluator then identifies the size of the maximum inscribed sphere for each pore voxel and determines PSD of the fine image by counting the number of similarly sized pore voxel.

At block 211, the model evaluator runs a flow simulation on the fine grain model obtained at block 209. The model evaluator simulates single or multiphase flow of the digital porous plate experiment, including fluid transport and distribution, by coupling semi-analytical solutions for individual elements. The model evaluator uses a simulation method that use numerical analysis and data structures to solve simplified kinetic equations and directly simulates the fundamental equations of flow. The Lattice-Boltzmann method (LBM) is a simulation method that the model evaluator can use to simulate flow and will be used to describe the simulation method used throughout the operations. LBM is used illustratively and in no way limits other simulation methods that may be used to characterize fundamental equations of flow. Simulation methods include LBM coupled with finite-volume method (FVM), finite-element method (FEM), finite-difference method (FDM), and various combinations thereof. Using LBM, the model evaluator simulates the macroscopic state of a fluid of the Darcy region, such as the volumetric fluid flow and absolute permeability, and solves the generalized Boltzmann Transport Equation (BTE) or various derivations of the BTE to characterize the model. The boundary conditions used in LBM are dependent on the intrinsic property of the solid and fluid in the Darcy regions as well as the pressure distribution surrounding the region. Therefore, the boundary conditions may change for each portion of the Darcy region selected. By simulating the flow of the digital porous plate experiment, the model evaluator generates a water and oil distribution on the fine grain image for each capillary pressure $P_c$ or water saturation $S_w$.

At block 213 the model evaluator substitutes the flow simulation results from block 211 into the corresponding Darcy region of the coarse grain model. The model evaluator substitutes at least one of porosity, absolute permeability, capillary pressure and, relative permeability of water and oil parameters with the Darcy region. The model evaluator fits the parameters obtained from the finer resolution model (smaller voxels) into a coarser resolution model (with larger voxels) through upscaling. In upscaling, the model evaluator assigns each larger voxel subdomain to a smaller voxel through discretization algorithms and calculates the parameters of each subdomain using the solutions of the finer scale LBM simulation (local solutions) corresponding to the smaller voxel. If a non-LBM simulation is used at block 211, the model evaluator calculates the parameters of each subdomain using analogous upscaling methods using similar local solutions from the non-LBM simulation.

At block 215, the model evaluator determines whether there is an additional Darcy region from block 205. If there is an additional Darcy region, control returns to block 205 for the next Darcy region.

At block 217, the model evaluator removes contributions due to overlapped pores. The model evaluator removes extra contribution from overlapping pores by converting small pore regions from the coarse grain model into under-resolved Darcy regions. Small pores are defined as pores with radius less than a few voxels in size. Transforming the small pores into Darcy regions prevents the pore regions smaller in size (regions most likely to be overlapped) from contributing to both the fine and coarse resolutions simulations. The small pores, though segmented as pore region, were already poorly resolved in the coarse scale and therefore their removal would not degrade the accuracy. Model evaluator also improves the accuracy of the fine scale simulation by this transformation. By removing small pore regions from the coarse model, the model evaluator increases the smallest pore radius of the overlapping pores, $r_c$, in the coarse scale simulation. The model evaluator simulates the removed small pores in the fine scale with better resolution. Therefore, the model evaluator improves the accuracy of simulation of these small pores. If the converted pore region is not found in any existing Darcy regions, the model evaluator adds a Darcy region for the converted pore region. The model evaluator then determines the map functions of the converted pore region that describe the flow properties, such as absolute permeability, capillary pressure and relative permeability of the added Darcy region. The porosity is assumed to be 1 as it was initially a pore region. The water saturation of the pore, $S_w$, is assumed to be either 0 or 1. The absolute permeability is given by Equation 1a wherein r is the radius of the pore region converted.

$$k = \frac{r^2}{8} \tag{1a}$$

The model evaluator determines the capillary pressure $P_c$ given by Equation 1b where σ is the interfacial tension between water and oil and θ is the water contact angle.

$$S_w = 1, \text{ as } P_c \leq \frac{2\sigma\cos(\theta)}{r}, \tag{1b}$$
$$S_w = 0, \text{ as } P_c \geq \frac{2\sigma\cos(\theta)}{r}.$$

The model evaluator determines the water relative permeability $k_w$ given by Equation 1c.

$k_w = 1$, as $S_w = 1$, $k_w = 0$, as $S_w = 0$. \hfill (1c)

The model evaluator determines the oil relative permeability $k_o$ given by Equation 1d.

$k_o=0$, as $S_w=1$, $k_o=1$, as $S_w=0$. (1d)

The model evaluator then substitutes the determined flow properties of the converted pore region into the coarse model.

At block 219, the model evaluator runs a flow simulation on the coarse scale model with substituted flow simulation and overlapping pore correction results. Map functions for Darcy regions from block 203 have been determined and upscaled into the coarse scale model through blocks 205-215. Map functions for the converted small pore regions have also been resolved through block 217. The model evaluator runs a flow simulation analogous to the operation described at block 211 to determine the capillary pressure and relative permeability of the multiscale heterogeneous rock.

Figure 3:
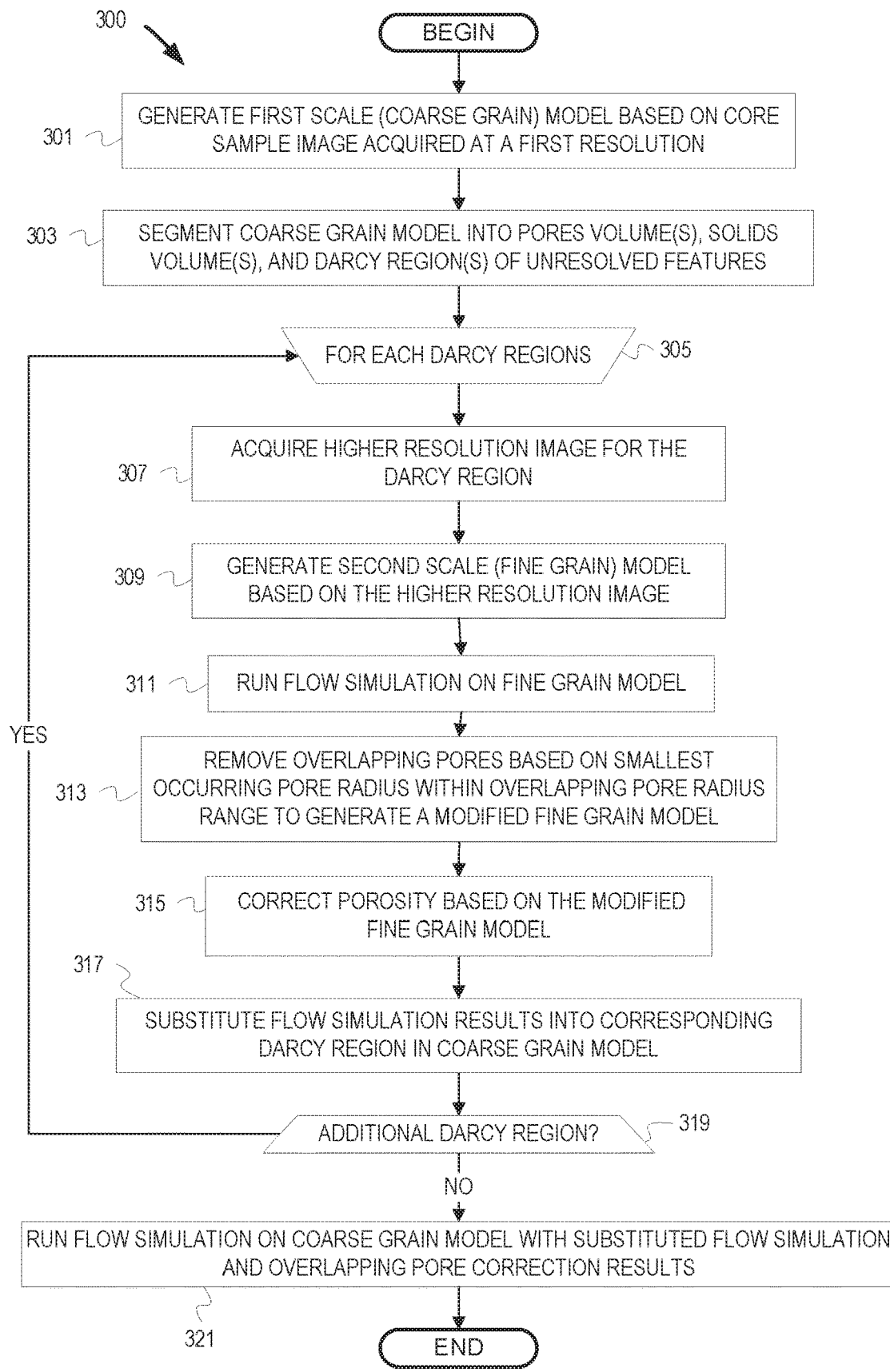
FIG. 3 depicts a flowchart of operations for multiscale modeling that removes the effect of overlapping pores for multiscale heterogeneous core formation by removing extra porosity of a fine grain image in overlapped pores

FIG. 3 depicts a flowchart 300 of operations for multiscale modeling that removes the effect of overlapping pores for multiscale heterogeneous core formation by removing extra porosity of a fine grain image in overlapped pores. The initial blocks are similar to those in FIG. 2. For instance, blocks 301, 303, 305, 307, 309, 311 are similar to blocks 201, 203, 205, 207, 209, 211.

At block 313, the model evaluator removes the overlapping pores in the fine grain model to generate a modified fine grain model. The model evaluator uses the PSD of the rough grain model generated at block 303 and PSD of the fine grain model generated at block 309 to identify the range of pore size radius that overlap between the fine grain model and the coarse grain model. The range is bounded by $r_{min}$ of the coarse grain model and $r_{max}$ of the fine grain model. The smallest occurring pore radius within that range ($r_c$) is chosen. The model evaluator generates a modified fine grain model by removing the pore regions that have pore radiuses above the $r_c$ from the fine grain model. By removing the overlapped pores from the fine grain model, the model evaluator corrects the error arising from double counting.

At block 315, the model evaluator corrects the porosity of the fine grain model based on the modified fine grain model. The model evaluator determines a corrected porosity by summing the pore volumes in the modified fine grain model that now only has pore volumes with radius smaller than $r_c$. The model evaluator replaces the old porosity value, obtained during flow simulation result at block 311, with the corrected porosity.

The operations performed by the model evaluator as represented by blocks 317, 319, and 321 are similar to those represented in blocks 213, 215 and block 219 to obtain capillary pressure and the relative permeability of the core sample. In contrast to FIG. 2, the example operations of FIG. 3 remove the contribution from overlapping as each Darcy region is processed.

Figure 4:
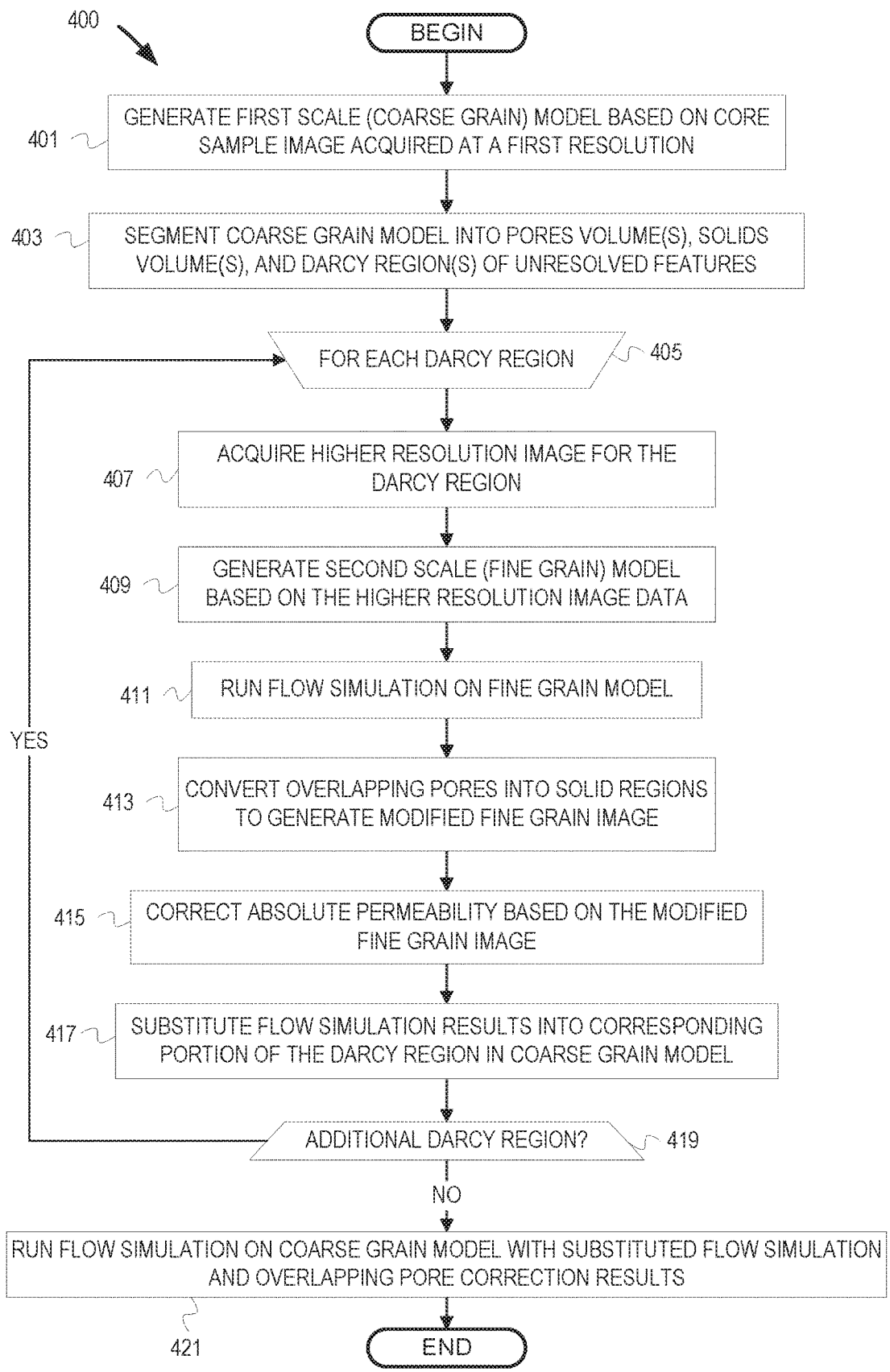
FIG. 4 depicts a flowchart of operations for multiscale modeling that removes the effect of overlapping pores for multiscale heterogeneous core formation by correcting the absolute permeability.

FIG. 4 depicts a flowchart 400 of operations for multiscale modeling that removes the effect of overlapping pores for multiscale heterogeneous core formation by correcting the absolute permeability. The initial blocks 401, 403, 405, 407, 409, 411 are similar to blocks 201, 203, 205, 207, 209, 211.

At block 413, the model evaluator converts overlapping pores in the fine grain image into solid regions. Similar to block 313 of FIG. 3, the model evaluator determines $r_c$ within the range of overlapping pore radiuses of the fine and coarse grain models. The model evaluator then transforms the pore regions in the fine grain image above the $r_c$ into solid regions. The modified fine grain image replaces the fine grain image for subsequent operations.

At block 415, the model evaluator corrects the absolute permeability based on the modified fine grain image. The model evaluator determines a corrected absolute permeability by using the relationship between the area of solid regions and absolute permeability. The model evaluator approximates the corrected absolute permeability from the trend between the increase in the area of solid region in the modified fine grain image and absolute permeability. The model evaluator then replaces the absolute permeability value with the corrected absolute permeability. In another embodiment, block 413 may be performed prior to block 411. Once the flow simulation is run, the corrected absolute permeability can be obtained. The example operations depicted in blocks 417, 419, 421 are similar to those depicted in blocks 317, 319, 321 of FIG. 3.

Figure 5A:
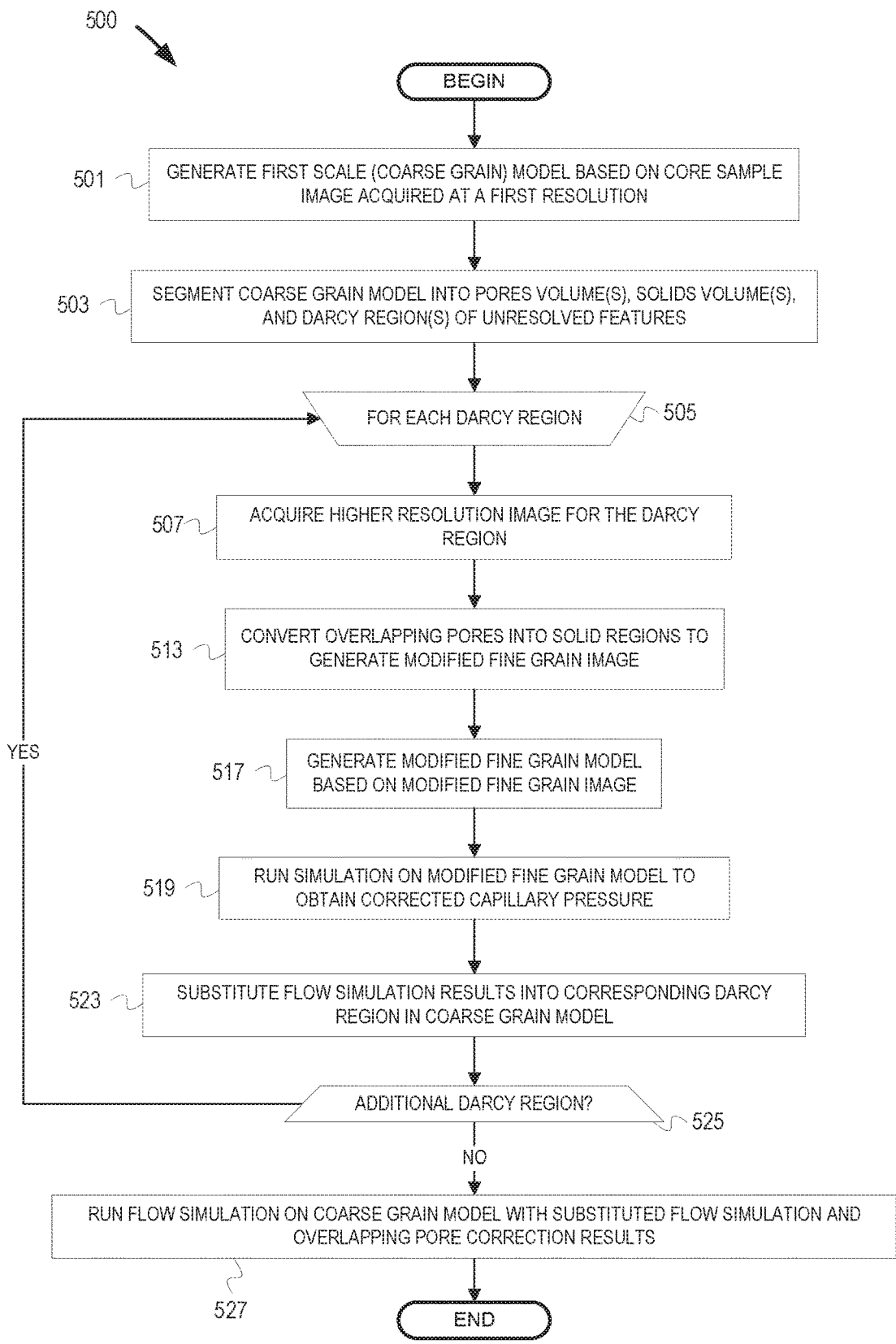
FIG. 5A depicts a flowchart of operations for a first multiscale modeling that removes the effect of overlapping pores for multiscale heterogeneous core formation by correcting the capillary pressure.

FIG. 5A depicts a flowchart 500 of operations for a first multiscale modeling that removes the effect of overlapping pores for multiscale heterogeneous core formation by correcting the capillary pressure. The initial blocks 501, 503, 505, 507 are similar to blocks 401, 403, 405, 407.

At block 513, the model evaluator converts overlapping pores in the fine grain image into solid regions to generate a modified fine grain image. The model evaluator identifies overlapping pores in a manner analogous to block 413 by using the PSD of the rough grain model and PSD of the fine grain model and determining the $r_c$.

At block 517, the model evaluator generates a modified fine grain model based on the modified fine grain image. The model evaluator generates the fine grain model in a manner similar to operations described at blocks 201 and 203. The model evaluator generates the model by simulating fluids, such as oil and water, to flow in the pores and Darcy region according to the governing equations of fluid mechanics and the map functions. The model evaluator identifies the pore sizes in the updated fine image.

At block 519, the model evaluator runs a flow simulation on the modified fine grain model to obtain a corrected capillary pressure. The model evaluator uses operation analogous to block 411 to simulate multiphase flow. By simulating the multiphase flow of the digital porous plate experiment, the model evaluator generates a water and oil distribution of the modified fine grain image. The model evaluator uses the water and oil distribution of the modified fine grain image to calculate the corrected capillary pressure as a function of water saturation.

At blocks 523, 525, 527, the model evaluator performs operations analogous to blocks 417, 419, 421 to obtain capillary pressure and the relative permeability of the core sample.

Figure 5B:
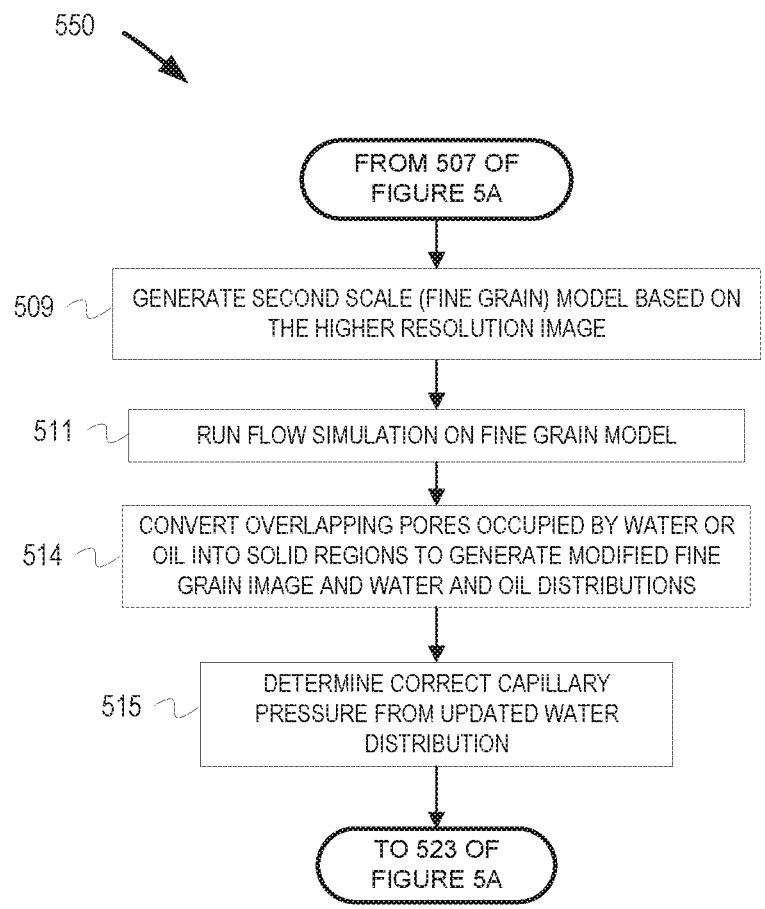
FIG. 5B depicts a flowchart of operations for a second multiscale modeling that removes the effect of overlapping pores for multiscale heterogeneous core formation by correcting the capillary pressure.

FIG. 5B depicts a flowchart 550 of example operations for a second multiscale modeling that removes the effect of overlapping pores for multiscale heterogeneous core formation by correcting the capillary pressure. FIG. 5B has different example operations represented by blocks 509, 511, 514, and 515 instead of the example operations represented by blocks 513, 517, and 519 depicted in FIG. 5A. The example operations represented by blocks 509 and 511 are similar to the example operations represented by blocks 409 and 411 and will not be described again.

At block 514, the model evaluator converts the overlapping pores in the fine grain image that are occupied by water or oil to solid. The model evaluator identifies overlapping pores in a manner analogous to block 413 by using the PSD of the rough grain model and PSD of the fine grain model and determining the $r_c$. The model evaluator obtains the updated water and oil distributions for the modified core sample.

At block 515, the model evaluator determines the water saturation for a certain capillary pressure by summing the volumes of pores occupied by the water and oil separately in the updated water and oil distributions determined at block 514. Then the model evaluator obtains updated capillary pressure as a function of water saturation.

At blocks 523, 525, 527, the model evaluator performs operations analogous to blocks 417, 419, 421 to obtain capillary pressure and the relative permeability of the core sample.

Figure 6A:
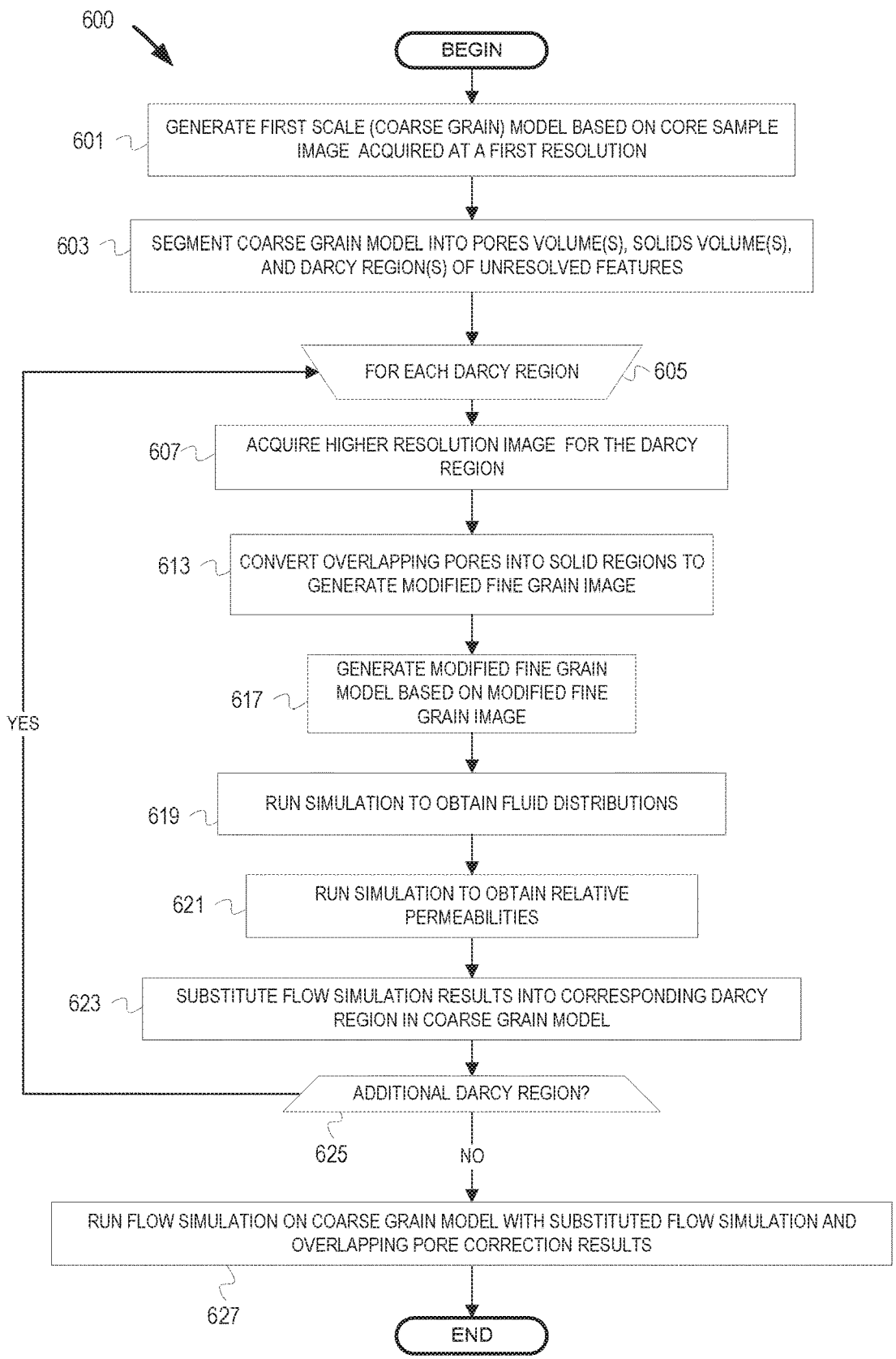
FIG. 6A depicts a flowchart of operations for a first multiscale modeling that removes the effect of overlapping pores for multiscale heterogeneous core formation by correcting the relative permeability.

FIG. 6A depicts a flowchart 600 of operations for a first multiscale modeling that removes the effect of overlapping pores for multiscale heterogeneous core formation by correcting the relative permeability. The initial blocks 601, 603, 605, 607, 613, 617 are similar to blocks 401, 403, 405, 407, 513, 517.

At block 619, the model evaluator simulates a digital porous plate experiment using operations similar to those of block 519 using a modified fine grain model, generated at block 617, based on the modified fine grain image. By simulating the multiphase flow of the digital porous plate experiment, the model evaluator generates a water and oil distribution of the modified fine grain image.

At block 621, the model evaluator runs flow simulations using the water and oil distributions obtained at block 619 to obtain corrected oil and water relative permeabilities. The relative permeability of water is given by Equation 2a where $k_w$ is the water relative permeability, k is the absolute permeability, and $k_{ew}$ is the effective water permeability.

$$k_w = \frac{k_{ew}}{k} \tag{2a}$$

The model evaluator runs a flow simulation with water filled regions as pore regions and oil filled regions as solid regions to obtain the effective water permeability over a range of fluid saturations. The model evaluator uses the effective water permeability to determine the relative water permeability corrected for overlapping. Similarly, the relative permeability of oil is given by Equation 2b where $k_o$ is the oil relative permeability, k is the absolute permeability, and $k_{eo}$ is the effective oil permeability.

$$k_o = \frac{k_{eo}}{k} \tag{2b}$$

The model evaluator runs a flow simulation with oil filled regions as pore regions and water filled regions as solid regions to obtain the effective oil permeability over a range of fluid saturations. The model evaluator uses the effective oil permeability to determine the relative oil permeability corrected for overlapping. At blocks 623, 625, 627, the model evaluator performs operations analogous to blocks 523, 525, 527 to obtain capillary pressure and the relative permeability of the core sample.

Figure 6B:
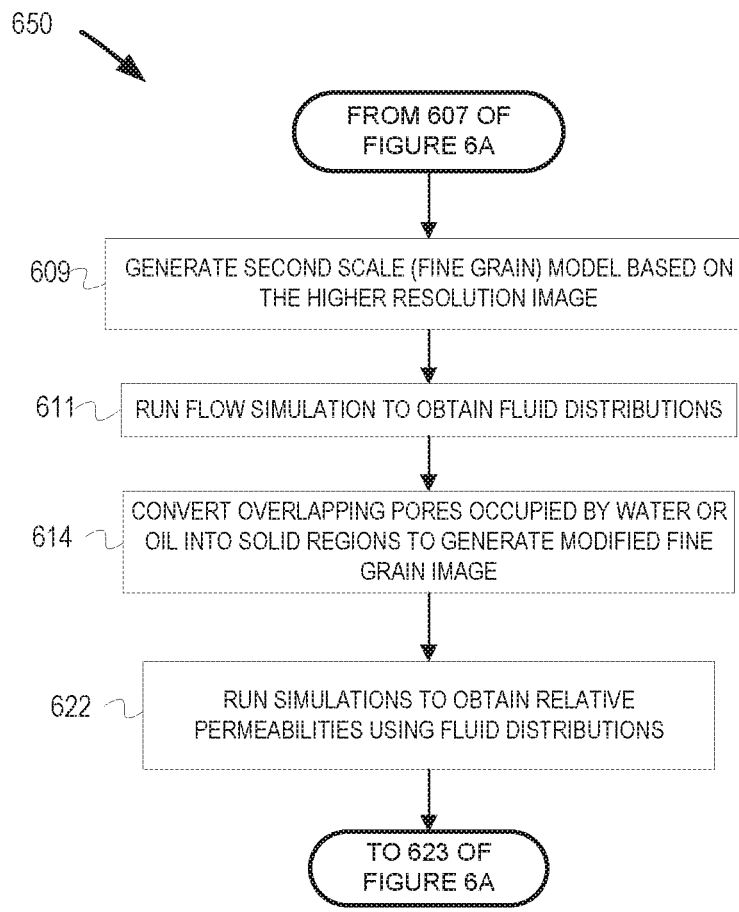
FIG. 6B depicts a flowchart of operations for a second multiscale modeling that removes the effect of overlapping pores for multiscale heterogeneous core formation by correcting the relative permeability.

FIG. 6B depicts a flowchart 650 of operations for a second multiscale modeling that removes the effect of overlapping pores for multiscale heterogeneous core formation by correcting the relative permeability. FIG. 6B has different example operations represented by blocks 609, 611, 614, and 622 instead of the example operations represented by blocks 613, 617, 619, and 621 depicted in FIG. 6A. The example operations represented by blocks 609 and 611 are similar to the example operations represented by blocks 409 and 411 and will not be described again.

At block 622, the model evaluator runs flow simulations using the water and oil distributions obtained at block 614 to obtain corrected oil and water relative permeabilities similar to operation described at block 622. At blocks 623, 625, 627, the model evaluator performs operations analogous to blocks 523, 525, 527 to obtain capillary pressure and the relative permeability of the core sample.

Figure 7:
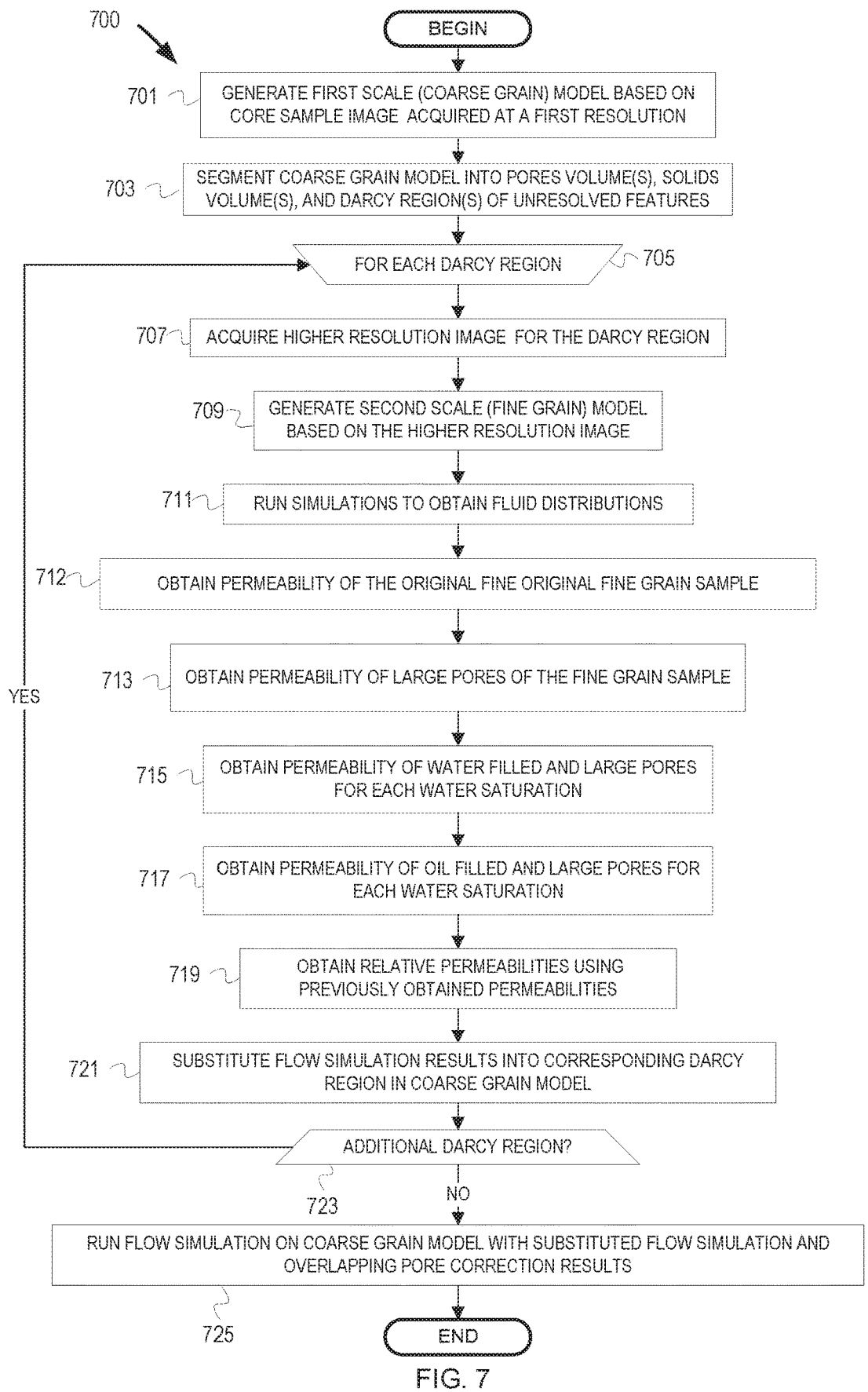
FIG. 7 depicts a flowchart of operations for a third multiscale modeling that removes the effect of overlapping pores for multiscale heterogeneous core formation by correcting the relative permeability.

FIG. 7 depicts a flowchart 700 of operations for a third multiscale modeling that removes the effect of overlapping pores for multiscale heterogeneous core formation by correcting the relative permeability. The initial blocks 701, 703, 705, 707, 709, 711 are similar to blocks 601, 603, 605, 607, 609, 611. At block 712, the model evaluator runs a flow simulation on the second scale model obtained at block 709 to obtain the absolute permeability of the core sample. The absolute permeability is denoted as k.

At block 713, the model evaluator obtains permeability of large pore regions. First, the model evaluator converts small pores in the higher resolution of the fine grain image into a solid region. For the conversion, the model evaluator obtains and uses the PSDs of the fine grain model generated at block 709 and the rough grain model generated at block 701 to determine $r_c$, the smallest occurring pore radius in the overlapping pore size range. The model evaluator then transforms the pore regions having a radius smaller than $r_c$ into solid regions in the fine grain image. The model evaluator obtains an absolute permeability of large pore regions by running a multiphase flow simulation on the modified fine image. The absolute permeability of large pore regions is denoted as $k(r \geq rc)$. The absolute permeability is considered to be zero for pore regions that are not connected.

At block 715, the model evaluator obtains the permeability of the water filled and large pores for each water saturation for each capillary pressure or water saturation in the digital porous plate experiment done at block 711. The model evaluator converts water occupied pore regions with a radius greater than or equal to $r_c$ into pore regions in the fine grain images with fluid distributions produced at block 711. The model evaluator converts oil occupied pore regions with a radius smaller than $r_c$ into solid regions in the same fine grain images. The model evaluator obtains absolute permeability by running multiphase flow simulations on each of these modified fine images. The obtained permeability is denoted as $k(w_p$ and $r \geq r_c)$, where $w_p$ represents a water filled condition. At block 717, the model evaluator obtains the permeability of oil filled and large pores by the similar operations at block 715. The model evaluator converts oil occupied pore regions with a radius greater than or equal to $r_c$ into pore regions in the fine grain images with fluid distributions produced at block 711. The model evaluator converts water occupied pore regions with a radius smaller than $r_c$ into solid regions in the same fine grain images. The model evaluator obtains an absolute permeability by running a multiphase flow simulation on each of these modified fine images. The obtained permeability is denoted as $k(o_p$ and $r \geq r_c)$, where $o_p$ represents an oil filled condition.

At block 719, the model evaluator obtains relative permeabilities using permeabilities previously obtained at blocks 712, 713, 715, and 717. The water relative permeability as a function of water saturation is obtained using Equation 3a, the oil relative permeability is obtained using Equation 3b.

$$k_w(s_w) = \frac{k(w_p \text{ and } r \geq r_c) - k(r \geq r_c)}{k - k(r \geq r_c)} \quad (3a)$$

$$k_o(s_w) = \frac{k(o_p \text{ and } r \geq r_c) - k(r \geq r_c)}{k - k(r \geq r_c)} \quad (3b)$$

At blocks 721, 723, 725, the model evaluator performs operations analogous to blocks 623, 625, 627 to obtain capillary pressure and the relative permeability of the core sample.

Figure 8:
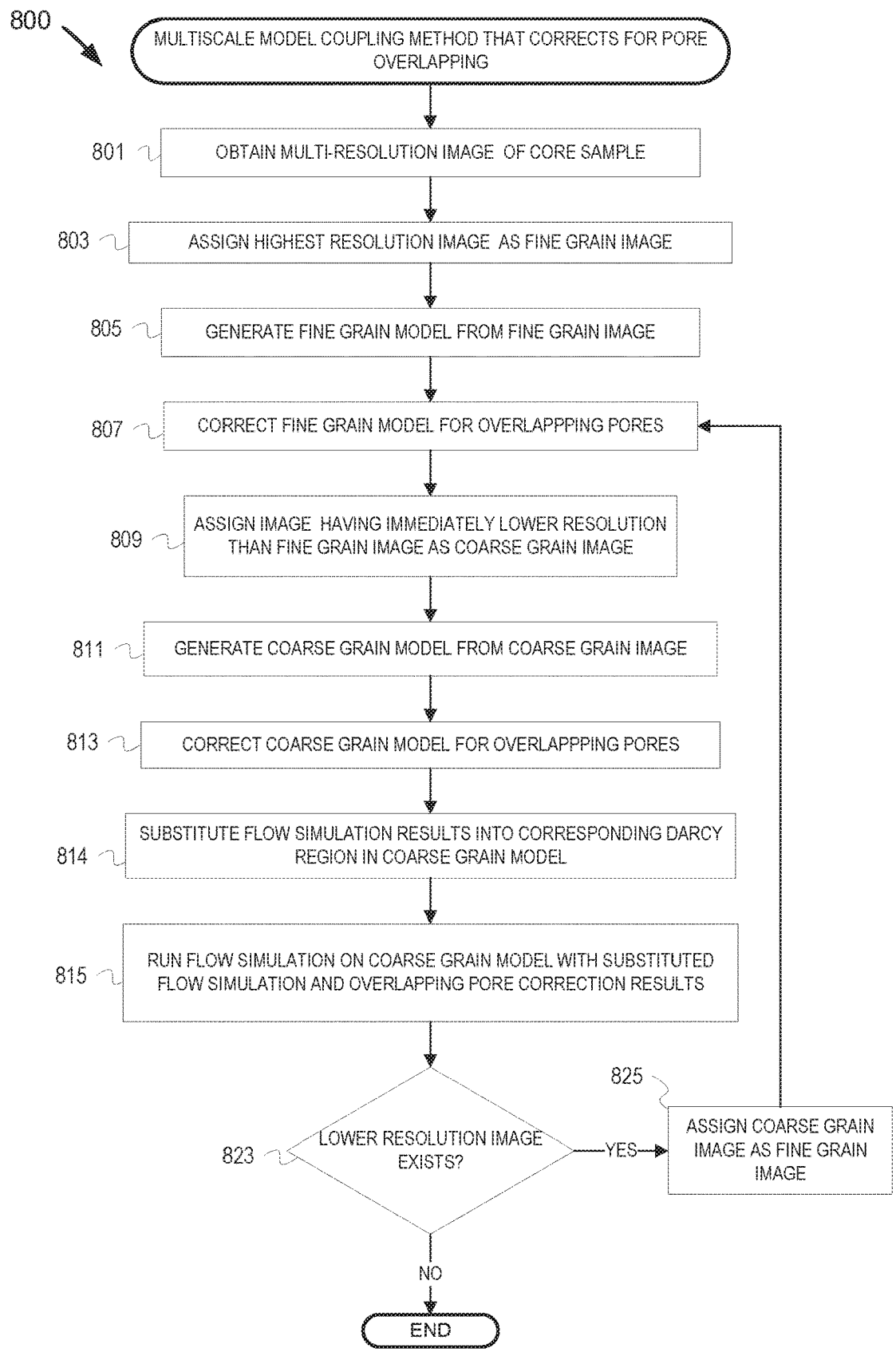
FIG. 8 depicts a general flowchart of operations for a multiscale model coupling method that corrects for pore overlapping.

FIG. 8 depicts a general flowchart 800 of operations for a multiscale model coupling method that corrects for pore overlapping.

At block 801, the model evaluator obtains multi-resolution image of a core sample. The model evaluator obtains multi-resolution images wherein the multi-resolution images consist of multiple core sample image similar to those described in FIG. 1. Each of the image have different resolutions and are imaged at different scales of measurements.

At block 803, the model evaluator assigns the image with the highest resolution as a fine grain image. At block 805, the model evaluator generates a fine grain model from the fine grain image in operation analogous to block 701. The fine grain model is separated into pore, solid and possible under-resolved regions. Pores and pore throats may be extracted from the image by various methods including but not limited to the erosion method, the medial axis (MA) method, and the maximal ball (MB) method.

At block 807, the model evaluator corrects the fine grain model for overlapping pores. Correction for overlapping pores may occur in the fine grain image before or after running a flow simulation on the fine grain model. The model evaluator uses a correction method analogous to that described in FIGS. 2-7.

At block 809, the model evaluator assigns from image having a resolution immediately lower than the fine grain image as a coarse grain image. At block 811, the model evaluator generates a coarse grain model from the coarse grain image in an operation analogous to block 805. At block 813, the model evaluator corrects the coarse grain model for overlapping pores. Correction for overlapping pores occurs here before running a flow simulation on the coarse grain model. The model evaluator uses a correction method described at block 217. At block 814, the model evaluator substitutes flow simulation results from fine grain model into a corresponding Darcy region in the coarse grain model. The model evaluator performs operation analogous to block 721. At block 815, the model evaluator runs a multiphase flow simulation on the coarse grain model similar to block 711.

At block 823, the model evaluator determines whether there is in the multi-resolution image an image having a lower resolution than the coarse grain image. At block 835, if there is an image having a lower resolution than the coarse grain image, the model evaluator assigns the coarse grain image as the fine grain image and proceeds back to block 807.

Example Computer

Figure 9:
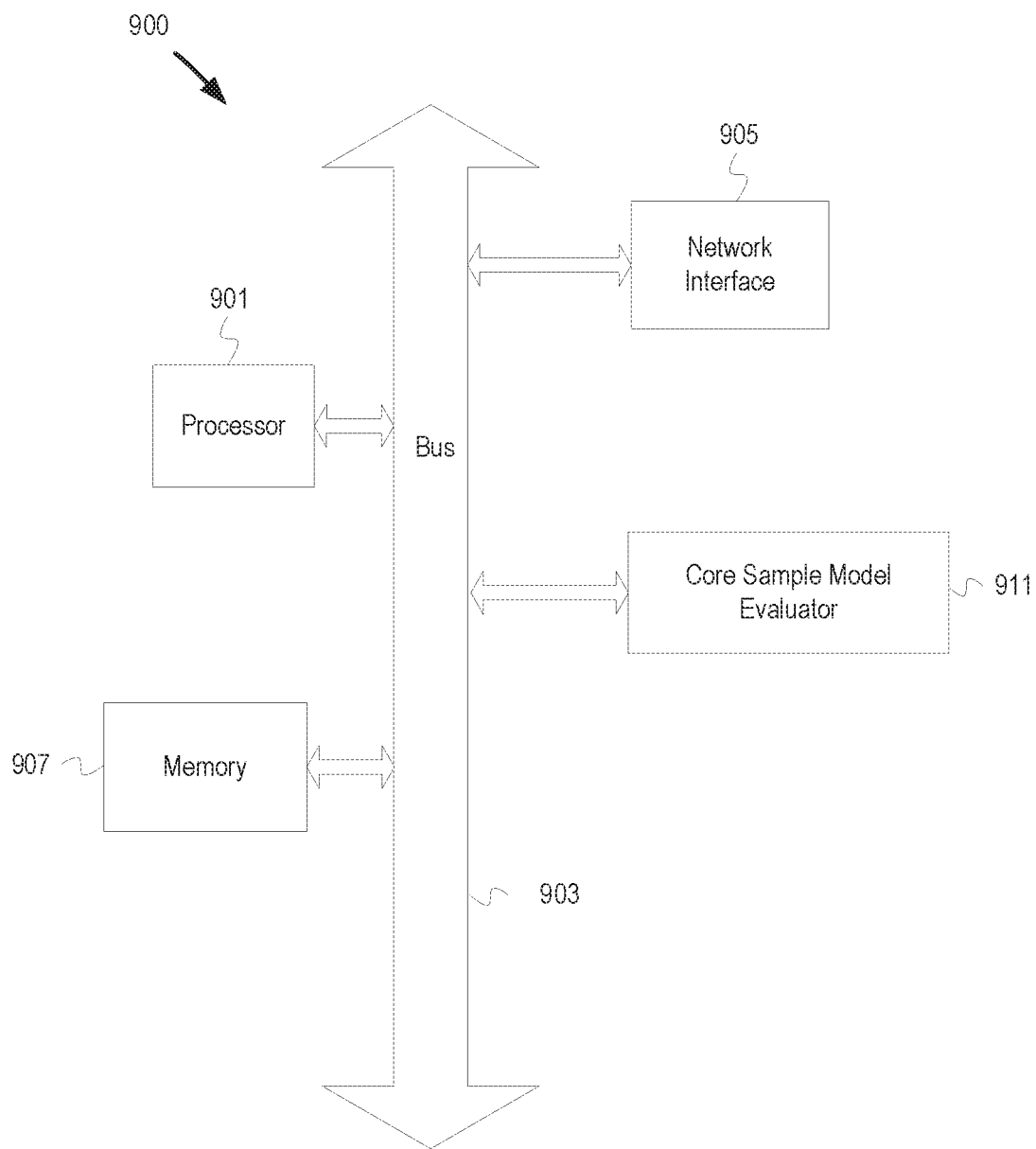
FIG. 9 depicts an example computer, according to some embodiments

FIG. 9 depicts an example computer, according to some embodiments. The computer includes a processor 901 (possibly including multiple processors, multiple cores, multiple nodes, and/or implementing multi-threading, etc.). The computer includes memory 907. The memory 907 may be system memory (e.g., one or more of cache, static random access memory (SRAM), dynamic random access memory (DRAM), zero capacitor random access memory (RAM), Twin Transistor RAM, enhanced dynamic random access memory (eDRAM), extended data output (EDO) RAM, double data rate (DDR) RAM, electrically erasable programmable read-only memory (EEPROM), nano-random access memory (NRAM), resistive random access memory (RRAM), silicon-oxide-nitride-oxide-silicon (SONOS), parameter random access memory (PRAM), etc.) or any one or more of the above already described possible realizations of machine-readable media. The computer system also includes a bus 903 (e.g., peripheral component interconnect (PCI), industry standard architecture (ISA), PCI-Express, HyperTransport® bus, InfiniBand® bus, NuBus, etc.) and a network interface 905 (e.g., a Fiber Channel interface, an Ethernet interface, an internet small computer system interface, synchronous optical networking (SONET) interface, wireless interface, etc.).

The computer also includes a core sample model evaluator 911. The core sample model evaluator 911 can generate core sample models and modified core sample models, as described above using various methods including LBM. The core sample model evaluator 911 can perform various simulations, calculations, and operations on the sample model generated. For example, the core sample model evaluator 911 can be used to obtain opening map of the core sample using Minkowski functions and perform digital porous plate technique on the core sample at various scales and resolutions. Any one of the previously described functionalities may be partially (or entirely) implemented in the hardware and/or on the processor 901. For example, the functionality may be implemented with an application specific integrated circuit, in logic implemented in the processor 901, in a co-processor on a peripheral device or card, etc. Further, realizations may include fewer or additional components not illustrated in FIG. 9 (e.g., video cards, audio cards, additional network interfaces, peripheral devices, etc.). The processor 901 and the network interface 905 are coupled to the bus 903. Although illustrated as being coupled to the bus 903, the memory 907 may be coupled to the processor 901.

It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus for execution to implement the various methods described above. As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platforms (operating system and/or hardware), application ecosystems, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a RAM, a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as the Java® programming language, C++ or the like, a dynamic programming language such as Python, a scripting language such as Perl programming language or PowerShell script language, and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Using the apparatus, systems, and methods disclosed herein may provide the ability to more efficiently evaluate the formation and its features.

While the aspects of the disclosure are described with reference to various implementations and exploitations, it will be understood that these aspects are illustrative and that the scope of the claims is not limited to them. In general, techniques for processing and analyzing of particles from downhole as described herein may be implemented with facilities consistent with any hardware system or hardware systems. Many variations, modifications, additions, and improvements are possible.

Plural instances may be provided for components, operations, or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

EXAMPLE EMBODIMENTS

Example embodiments include the following:

Embodiment 1: A method comprising: for a region of unresolved formation features in a first model that is based on first resolution image data, obtaining multi-phase flow simulation results for a second model that is based on second resolution image data, wherein the first and second resolution image data correspond to a core sample from a formation and the first resolution image data is at a lower resolution than the second resolution image data; correcting for pore overlapping between the first and the second models; substituting, for the region of unresolved formation features, multi-phase flow simulation results of the second model based on the correcting for pore overlapping; and determining capillary pressure and relative permeability of the formation with the first model after the substituting.

Embodiment 2: The method of Embodiment 1, wherein the second resolution image data that is at a higher resolution than the first resolution image data corresponds to at least the region of unresolved formation features.

Embodiment 3: The method of Embodiments 1 or 2 further comprising determining a range of pore radiuses that overlap between the first and the second model and determining a smallest pore radius $r_c$ that occurs in at least one of the models within the range.

Embodiment 4: The method of Embodiment 3, wherein correcting for pore overlapping comprises identifying in the second model a region of pores with a pore radius greater than $r_c$ and converting the region into a solid region.

Embodiment 5: The method of Embodiment 3, wherein correcting for pore correction comprises removing from the second model pores having a radius greater than $r_c$.

Embodiment 6: The method of Embodiment 3, wherein correcting for pore correction comprises recharacterizing from the first model pores having a radius smaller than $r_c$ as unresolved formation features.

Embodiment 7: The method of any one of Embodiments 1-6, wherein substituting, for the region of unresolved formation features, multi-phase flow simulation is comprised of relative water permeability and relative oil permeability simulation result.

Embodiment 8: The method of any one of Embodiments 1-7 further comprising running the multi-phase flow simulation on the first model with the substituted multi-phase flow simulation results.

Embodiment 9: The method of Embodiments 1-8 further comprising: obtaining the core sample from the formation with a coring tool; and scanning the core sample with a computerized tomography scanner to obtain the first resolution image data and the second resolution image data.

Embodiment 10: The method of Embodiments 1-9, wherein the core sample includes one or more drill cuttings.

Embodiment 11: A non-transitory, computer-readable medium having instructions stored thereon that are executable by a computing device to perform operations comprising: generating a model of a core sample from a formation; identifying pore size of the core sample based, at least in part, by obtaining an opening map of the model; identifying overlapping pores in the model that are resolved in both a coarse scale image of the core sample and in a fine scale image of the core sample; removing the overlapping pores in the model to generate a modified core sample model; and calculating a map function of capillary pressure and relative permeability of the formation based at least in part on the modified core sample model.

Embodiment 12: The non-transitory, computer-readable medium of Embodiment 11, wherein removing the overlapping pores in the model to generate a modified core sample model is comprised of converting pores with radius smaller than a threshold radius into under-resolved Darcy region to generate a modified core sample model.

Embodiment 13: The non-transitory, computer-readable medium of Embodiments 11 or 12, wherein calculating the map function of the capillary pressure comprises at least in part of performing a single scale digital porous plate technique on the modified core sample model.

Embodiment 14: The non-transitory, computer-readable medium of any one of Embodiments 11-13, wherein calculating the map function of the capillary pressure is comprised at least in part of obtaining a water and oil distributions for the core sample model, converting overlapping pores occupied by water or oil to solid, and obtaining water saturation from a modified water distribution resulting from the conversion of overlapping pores.

Embodiment 15: The non-transitory, computer-readable medium of any one of Embodiments 11-14, wherein calculating the relative permeability of the core sample is comprised at least in part of determining a capillary pressure function of the water and oil distribution of the original core sample model and transforming regions of water and oil that are smaller than the smallest radius of the overlapping pores.

Embodiment 16: The non-transitory, computer-readable medium of any one of Embodiments 11-15, wherein generating the model of the core sample is further comprised of simulating a two-phase flow in a representative volume of the core sample using a dynamic multi-scale lattice-Boltzmann method simulator.

Embodiment 17: The non-transitory, computer-readable medium of any one of Embodiments 11-16, wherein obtaining an opening map of the model is comprised of using Minkowski functions.

Embodiment 18: The non-transitory, computer-readable medium of any one of Embodiments 11-17, wherein removing overlapping pores in the model is further comprised of summing a pore size distribution fraction of pores with radius smaller than a threshold radius of the overlapping pores for porosity in the fine scale image.

Embodiment 19: A system comprising: a computerized tomography scanner to scan a core sample and to generate a coarse scale image and a fine scale image of the core sample; a processor; and a machine-readable medium having instructions stored thereon that are executable by the processor to cause the processor to, generating a model of the core sample based, at least in part, on the coarse scale image and the fine scale image; identify pore size of the core sample based, at least in part, on an opening map of the model; identify overlapping pores in the model that are resolved in both the coarse scale image of the core sample and in the fine scale image of the core sample; remove the overlapping pores in the model to generate a modified core sample model; and calculate a map function of capillary pressure and relative permeability of a formation represented by the core sample based, at least in part, on the modified core sample model.

Embodiment 20: The system of Embodiment 19, further comprising a coring tool to obtain the core sample from the formation.

Embodiment 21: The system of Embodiments 19 or 20, wherein the instructions to remove the overlapping pores in the model to generate a modified core sample model comprise of instructions to convert pores with radius smaller than a threshold radius into under-resolved Darcy region to generate a modified core sample model.

Embodiment 22: The system of any one of Embodiments 19-21, wherein the instructions to calculate the map function of the capillary pressure and relative permeability comprise instructions to perform a single scale digital porous plate technique on the modified core sample model.

Embodiment 23: The system of any one of Embodiments 19-22, wherein the instructions to calculate the map function of the capillary pressure and relative permeability is comprised at least in part of instructions to obtain water and oil distributions for the core sample model and to obtain water saturation from a modified water distribution, wherein the instructions to remove the overlapping pores comprise instructions to convert those of the overlapping pores occupied by water or oil to solid, wherein the modified water distribution results from the conversion of overlapping pores.

What is claimed is:

1. A method comprising:
for a region of unresolved formation features in a first model that is based on first image data, obtaining multi-phase flow simulation results for a second model that is based on second image data, wherein the first and second image data correspond to a core sample from a formation and the first image data is at a lower resolution than the second image data;
identifying an overlapping pore that is resolved in both the first and second model, wherein the overlapping pore resides at a first spatial location in the first image data and at the first spatial location in the second image data;
removing an effect of the overlapping pore between the first and the second models;
substituting, for the region of unresolved formation features, multi-phase flow simulation results of the second model after removing the effect of the overlapping pore; and
determining capillary pressure and relative permeability of the formation with the first model after the substituting.

2. The method of claim 1, wherein the second image data that is at a higher resolution than the first image data corresponds to at least the region of unresolved formation features.

3. The method of claim 1 further comprising determining a range of pore radiuses that overlap between the first and the second model and determining a smallest pore radius $r_c$ that occurs in at least one of the models within the range.

4. The method of claim 3, wherein removing the effect of the overlapping pore comprises identifying in the second model a region of pores with a pore radius greater than $r_c$ and converting the region into a solid region.

5. The method of claim 3, wherein removing the effect of the overlapping pore comprises removing from the second model pores having a radius greater than $r_c$.

6. The method of claim 3, wherein removing the effect of the overlapping pore comprises recharacterizing from the first model pores having a radius smaller than $r_c$ as unresolved formation features.

7. The method of claim 1, wherein substituting, for the region of unresolved formation features, multi-phase flow simulation is comprised of relative water permeability and relative oil permeability simulation result.

8. The method of claim 1 further comprising running the multi-phase flow simulation on the first model with the substituted multi-phase flow simulation results.

9. The method of claim 1 further comprising:
obtaining the core sample from the formation with a coring tool; and
scanning the core sample with a computerized tomography scanner to obtain the first image data and the second image data.

10. The method of claim 1 wherein the core sample includes one or more drill cuttings.

11. A non-transitory, computer-readable medium having instructions stored thereon that are executable by a computing device to perform operations comprising:
generating a model of a core sample from a formation;
identifying pore size of the core sample based, at least in part, by obtaining an opening map of the model;
identifying an overlapping pore in the model that is resolved in both a coarse scale image of the core sample and in a fine scale image of the core sample, wherein the overlapping pore resides at a first spatial location in the coarse scale image and at the first spatial location in the fine scale image;
removing an effect of the overlapping pore in the model to generate a modified core sample model; and
calculating a map function of capillary pressure and relative permeability of the formation based at least in part on the modified core sample model.

12. The non-transitory, computer-readable medium of claim 11, wherein removing the effect of the overlapping pore in the model to generate a modified core sample model is comprised of converting pores with radius smaller than a threshold radius into under-resolved Darcy region to generate a modified core sample model.

13. The non-transitory, computer-readable medium of claim 11, wherein calculating the map function of the capillary pressure comprises at least in part of performing a single scale digital porous plate technique on the modified core sample model.

14. The non-transitory, computer-readable medium of claim 11, wherein calculating the map function of the capillary pressure is comprised at least in part of obtaining a water and oil distributions for the core sample model, converting the overlapping pore occupied by water or oil to solid, and obtaining water saturation from a modified water distribution resulting from the conversion of the overlapping pore.

15. The non-transitory, computer-readable medium of claim 11, wherein calculating the relative permeability of the core sample is comprised at least in part of determining a capillary pressure function of the water and oil distribution of the original core sample model and transforming regions of water and oil that are smaller than the smallest radius of the overlapping pore.

16. The non-transitory, computer-readable medium of claim 11, wherein generating the model of the core sample is further comprised of simulating a two-phase flow in a representative volume of the core sample using a dynamic multi-scale lattice-Boltzmann method simulator.

17. The non-transitory, computer-readable medium of claim 11, wherein obtaining an opening map of the model is comprised of using Minkowski functions.

18. The non-transitory, computer-readable medium of claim 11, wherein removing the effect of the overlapping pore in the model is further comprised of summing a pore size distribution fraction of pores with radius smaller than a threshold radius of the overlapping pore for porosity in the fine scale image.

19. A system comprising:
a computerized tomography scanner to scan a core sample and to generate a coarse scale image and a fine scale image of the core sample;
a processor; and
a machine-readable medium having instructions stored thereon that are executable by the processor to cause the processor to,
generating a model of the core sample based, at least in part, on the coarse scale image and the fine scale image;
identify pore size of the core sample based, at least in part, on an opening map of the model;
identify an overlapping pore in the model that is resolved in both the coarse scale image of the core sample and in the fine scale image of the core sample, wherein the overlapping pore resides at a first spatial location in the coarse scale image and at the first spatial location in the fine scale image;
remove an effect of the overlapping pore in the model to generate a modified core sample model; and
calculate a map function of capillary pressure and relative permeability of a formation represented by the core sample based, at least in part, on the modified core sample model.

20. The system of claim 19, further comprising a coring tool to obtain the core sample from the formation.

21. The system of claim 19, wherein the instructions to remove the effect of the overlapping pore in the model to generate a modified core sample model comprise of instructions to convert pores with radius smaller than a threshold radius into under-resolved Darcy region to generate a modified core sample model.

22. The system of claim 19, wherein the instructions to calculate the map function of the capillary pressure and relative permeability comprise instructions to perform a single scale digital porous plate technique on the modified core sample model.

23. The system of claim 19, wherein the instructions to calculate the map function of the capillary pressure and relative permeability is comprised at least in part of instructions to obtain water and oil distributions for the core sample model and to obtain water saturation from a modified water distribution, wherein the instructions to remove the overlapping pore comprise instructions to convert those of the overlapping pore occupied by water or oil to solid, wherein the modified water distribution results from the conversion of overlapping pore.

\* \* \* \* \*